US012629467B2

(12) United States Patent
Schenk

(10) Patent No.: US 12,629,467 B2
(45) Date of Patent: May 19, 2026

(54) METHOD FOR OPERATING A FLUID PUMP, AND OPHTHALMOSURGICAL SYSTEM WITH SAME

(71) Applicant: Carl Zeiss Meditec AG, Jena (DE)

(72) Inventor: Alexander Schenk, Frankehardt (DE)

(73) Assignee: Carl Zeiss Meditec AG, Jena (DE)

( * ) Notice: Subject to any disclaimer, the term of this patent is extended or adjusted under 35 U.S.C. 154(b) by 882 days.

(21) Appl. No.: 17/734,062

(22) Filed: Apr. 30, 2022

(65) Prior Publication Data

US 2022/0347375 A1 Nov. 3, 2022

(30) Foreign Application Priority Data

Apr. 30, 2021 (DE) ..................... 10 2021 111 178.1

(51) Int. Cl.
*A61M 3/02* (2006.01)
*A61F 9/007* (2006.01)

(52) U.S. Cl.
CPC ........ *A61M 3/0216* (2014.02); *A61M 3/0201* (2021.05); *A61F 9/00745* (2013.01); *A61M 2205/0216* (2013.01); *A61M 2205/332* (2013.01); *A61M 2205/3327* (2013.01)

(58) Field of Classification Search
CPC .............. A61M 3/0216; A61M 3/0201; A61M 2205/0216; A61M 2205/332; A61M 2205/3327; A61F 9/00745
USPC ........................................................ 604/290
See application file for complete search history.

(56) References Cited

U.S. PATENT DOCUMENTS

| | | | | |
|---|---|---|---|---|
| 5,499,969 A | * | 3/1996 | Beuchat .................. | A61M 1/77 604/151 |
| 10,722,619 B2 | | 7/2020 | Kuebler et al. | |
| 2012/0232466 A1 | * | 9/2012 | Kuebler .............. | A61F 9/00745 604/35 |
| 2017/0216093 A1 | * | 8/2017 | Kuebler .............. | A61M 3/0216 |

FOREIGN PATENT DOCUMENTS

| | | |
|---|---|---|
| DE | 102016201297 B3 | 3/2017 |
| EP | 3021803 B1 | 12/2017 |

OTHER PUBLICATIONS

Office Action issued in German Patent Application No. DE 10 2021 111 178.1, dated Jan. 28, 2022 (from which this application claims priority) and English language translation thereof.

* cited by examiner

*Primary Examiner* — Andrew J Mensh
(74) *Attorney, Agent, or Firm* — Ewers IP Law PLLC; Falk Ewers

(57) ABSTRACT

A method for operating a fluid pump of an ophthalmosurgical system for conveying a treatment fluid is provided. The fluid pump has a pump chamber and a drive chamber separated from the latter with an elastic partition element and which is acted upon by a drive fluid. A position of the partition element is detected. The method includes subjecting the drive fluid to a first drive pressure, detecting a treatment fluid pressure present in the first position of the partition element, subjecting the drive fluid to a further drive pressure, at which the partition element adopts a further position, detecting the at least one further position of the partition element, and a further treatment fluid pressure present in this further position, and taking into account the treatment fluid pressures and drive pressures present in the respective positions account in the operation of the fluid pump.

8 Claims, 6 Drawing Sheets

FIG. 7

METHOD FOR OPERATING A FLUID PUMP, AND OPHTHALMOSURGICAL SYSTEM WITH SAME

CROSS REFERENCE TO RELATED APPLICATIONS

This application claims priority to German patent application DE 10 2021 111 178.1, filed Apr. 30, 2021, the entire content of which is incorporated herein by reference.

TECHNICAL FIELD

The disclosure relates to a method for operating a fluid pump of an ophthalmosurgical system. The fluid pump is configured to convey a treatment fluid and with which the treatment fluid is conveyed during the operation of the system, wherein the fluid pump has a pump chamber and a drive chamber, which is separated from the pump chamber with an elastic partition element, wherein the drive chamber is acted upon by a drive fluid and a position of the elastic partition element is detected with a position sensor. The disclosure further includes a method for operating an ophthalmosurgical system for treating an eye, wherein the ophthalmosurgical system has a console for receiving a treatment fluid, a cassette, insertable into the console, for conveying the treatment fluid to a surgical instrument for treating the eye, and at least one fluid pump for conveying the treatment fluid during operation of the system, wherein the fluid pump has a pump chamber and a drive chamber, which is separated from the pump chamber with an elastic partition element, wherein the drive chamber is acted upon by a drive fluid and a position of the elastic partition element is detected with a position sensor, wherein the console has the drive chamber and the cassette has the pump chamber with the partition element. The disclosure finally also relates to an ophthalmosurgical system for treating an eye.

BACKGROUND

Ophthalmosurgical systems, methods for their operation and methods for operating fluid pumps are known in the prior art, and so in principle there is no need for separate documentary evidence of such systems and methods. Various surgical techniques are known for the treatment of a clouding of the crystalline lens, also known in medicine as cataract. The most widespread technique is phacoemulsification, in which a thin hollow needle is introduced into a capsular bag, in which the crystalline lens is arranged, and is induced to make ultrasonic vibrations. The lens can be emulsified with the vibrating hollow needle, and lens particles released in the process can be aspirated through an aspiration line with a pump. In the process, an irrigation fluid is delivered. The lens particles are aspirated, together with the fluid, as aspiration fluid. As soon as the lens has been completely emulsified and removed, a new artificial lens can be inserted into the then empty capsular bag. The treated patient can in this way recover good vision.

An advanced ophthalmosurgical system that has proven particularly suitable for phacoemulsification is described in DE 10 2016 201 297 B3, for example. In this system, two fluid pumps fluidically connected in parallel are used in each case for the irrigation and also for the aspiration. Each of the fluid pumps has a pump chamber, and a drive chamber separated from the pump chamber with an elastic partition element. For the intended operation of the fluid pump, the drive chamber is acted upon by a drive fluid whose drive pressure is varied for the performance of a respective pump stroke. Depending on this, a position of the elastic partition element thus changes, which correspondingly has an effect on the pump chamber. The pump chamber is acted upon by the respective treatment fluid, for example the irrigation fluid, the aspiration fluid or the like. The delivery action can then be achieved by suitably controlling an inlet valve and an outlet valve of the fluid pump.

A position of the elastic partition element is detected with a position sensor assigned to the respective fluid pump. A control device of the ophthalmosurgical system controls the function of the fluid pump at least depending on a sensor signal of the position sensor and on a drive pressure signal supplied with a drive pressure sensor. In addition, the control device can, for example, suitably control the inlet valve and the outlet valve.

By alternate actuation of the respective two fluid pumps connected in parallel, a volumetric flow with very little fluctuation can be obtained during a surgical procedure. In this way, an almost constant intraocular pressure can be obtained in the capsular bag. As long as sufficient irrigation fluid can be delivered, the system can be operated almost without interruption of the flow of irrigation fluid, even during a very lengthy surgical procedure.

The elastic partition element of a respective one of the fluid pumps is thus not actuated by a plunger or a rod but instead by the drive fluid. It is thus possible to achieve almost jolt-free and very rapid actuation. At the same time, the fluid pump embodied in this manner proves very reliable and requires very little maintenance. The ophthalmosurgical system described in DE 10 2016 201 297 B3 is therefore also particularly suitable for a method implementation that requires a reaction to a blockage of a needle tip of the hollow needle or of the aspiration opening. Such a state is also referred to as occlusion. With the ophthalmosurgical system described in DE 10 2016 201 297 B3, this situation can also be handled very effectively, and so an intraocular pressure can be kept almost constant even in the event of such operating disturbances.

For the intended operation of the ophthalmosurgical system, it is desirable to keep the intraocular pressure, particularly in the capsular bag, as constant as possible by regulating the pressure of the irrigation fluid and the vacuum of the aspiration fluid. For this purpose, it is desirable that the pressure of the treatment fluid be known as precisely as possible, so that correspondingly precise regulation of this pressure can be achieved. In the previously described fluid pump, the pressure of the treatment fluid depends on the drive pressure of the drive fluid. In addition, there is also a dependency on properties of the partition element. Deviations in properties between different partition elements may occur on account of component fluctuations and tolerances and also ageing effects resulting from storage or the like. These deviations may, for example, concern a dependency of a pressure difference, brought about by the partition element, on a respective position of the partition element. Such a deviation may lie above a desired precision range that is expedient for the regulation of the intraocular pressure.

SUMMARY

It is therefore an object of the disclosure to improve operation of an ophthalmosurgical system, and to improve an ophthalmosurgical system itself, in such a way that regulation in respect of the treatment liquid can be more precisely achieved.

The object is achieved by a method for operating a fluid pump of an ophthalmosurgical system, configured to convey the treatment fluid, a method for operating an ophthalmosurgical system for treating an eye, and an ophthalmosurgical system for treating an eye as described herein.

As regards a method of the type in question for operating a fluid pump of an ophthalmosurgical system, which fluid pump is configured to convey a treatment fluid, the disclosure proposes in particular that the drive fluid is subjected to a first drive pressure, at which the elastic partition element adopts a first position, a treatment fluid pressure present in the first position of the partition element is detected with a detection sensor of the ophthalmosurgical system, the drive fluid is subjected to at least one further drive pressure, which is different from the first drive pressure and at which the partition element adopts a further position different from the first position, the at least one further position of the partition element, brought about by the at least one further drive pressure, and a further treatment fluid pressure present in this further position are detected, and the treatment fluid pressures present in the respective positions and the drive pressures present in the respective positions are taken into account in the operation of the fluid pump.

As regards a method of the type in question for operating an ophthalmosurgical system for treating an eye, the disclosure proposes in particular that the method of the disclosure is started after the cassette has been inserted into the console.

As regards an ophthalmosurgical system of the type in question for treating an eye, the disclosure proposes in particular that the system at least includes:

a console for accommodating a treatment fluid container for receiving a treatment fluid, a cassette, insertable into the console, for steering the treatment fluid to a surgical instrument for treating the eye, at least one fluid pump for conveying the treatment fluid during operation of the system, wherein the fluid pump has a pump chamber and a drive chamber, which is separated from the pump chamber with an elastic partition element, wherein the drive chamber can be acted upon by a drive fluid and a position of the elastic partition element is detectable with a position sensor of the ophthalmosurgical system, wherein the ophthalmosurgical system is configured:

to subject the drive fluid to a first drive pressure, at which the elastic partition element adopts a first position, to detect a treatment fluid pressure present in the first position of the partition element with a detection sensor of the ophthalmosurgical system, to subject the drive fluid to at least one further drive pressure, which is different from the first drive pressure and at which the partition element adopts a further position different from the first position, to detect the at least one further position of the partition element, brought about by the at least one further drive pressure, and a further treatment fluid pressure present at this further position, and to take the treatment fluid pressures present in the respective positions and the drive pressures present in the respective positions into account in the operation of the fluid pump.

In particular, the ophthalmosurgical system according to an aspect of the disclosure is suitable for being able to carry out the methods according to the disclosure.

The disclosure is based, inter alia, on the concept that the function of the regulation for the treatment fluid can be improved if the properties of the fluid pump are known better and more precisely. This applies in particular to the properties of the partition element. Since the fluid pumps generally serve for conveying a medical treatment fluid, reasons of hygiene and reasons of sustainability often mean that no pressure sensors are provided for the treatment fluid. A conclusion regarding the pressure of the treatment fluid can therefore only be reached indirectly, that is to say depending on the drive pressure of the drive fluid. The actual pressure of the treatment fluid is not measured. It is therefore desirable to be able to take account of the specific properties of the partition element. With the method according to an aspect of the disclosure, it is possible for the regulation function to be more precise and therefore also more targeted.

For this purpose, by setting at least two mutually different drive pressures of the drive fluid, at least two mutually different positions are adopted. These positions can be detected with the position sensor. With a detection sensor of the ophthalmosurgical system, a respective pressure of the treatment fluid can be detected for these at least two drive pressures. The data thereby obtained can be evaluated in particular by the control device, such that in this way a behaviour of the partition element can be determined depending on a respective position. The behaviour typically concerns the fact that, in relation to the respective drive pressure, the partition element, depending on its respective position, can result in a pressure of smaller magnitude in the treatment fluid.

The knowledge of this dependency makes it possible to improve the regulation for the treatment fluid, for example the irrigation fluid or the aspiration fluid. The realization of the disclosure does not require the provision of expensive additional measures. Thus, the detection sensor for example can be made available by an element that is required for redundancy reasons, as will be explained in more detail below. The disclosure thus makes it possible to carry out the method individually for a respective fluid pump, even when a plurality of fluid pumps are fluidically connected in parallel, such that the method implementations according to an aspect of the disclosure and also the ophthalmosurgical system according to an aspect of the disclosure permit improved operation.

The partition element, which separates the pump chamber from the drive chamber, can be configured as an elastic membrane, a film or the like. Typically, a circumferential edge of the partition element can be arranged or secured fixedly in the fluid pump. In this way, the partition element can fluidically separate the pump chamber from the drive chamber, particularly in such a way that a sterility of the treatment fluid is not impaired.

For example, it is possible that the fluid pump is at least partially enclosed by the cassette and at least partially by the console. This makes it possible to connect the cassette to the console releasably, with the fluid pump being completed in their connected state. With the cassette, therefore, a replacement part can be made available which can serve to ensure a sterility of the ophthalmosurgical system for a respective surgical procedure on the eye, particularly as regards the treatment fluid. Thus, it is in fact possible that the treatment fluid only has to be guided through the cassette, and so the treatment fluid does not need to flow through the console. In this way, after a respective use of the ophthalmosurgical system, it is easily possible to restore the sterility of the ophthalmosurgical system by replacing the cassette. Of course, provision is typically made here that the cassette, in the state when connected to the console, is connected to the console in a fluid-tight manner, such that the respective drive chamber of the respective fluid pump adjoins the partition element in a fluid-tight manner, in order to be able to operate the fluid pump in the intended manner. For example, provision can thus be made that the cassette, in particular also the fluid pump or the cassette-side elements of the fluid pump, in particular the respective partition element, can be produced from a suitable plastic or comparable material.

The drive fluid, which serves to act on the drive chamber in order to be able to drive the fluid pump, can be for example a liquid, for example water, oil, mixtures of liquids and/or the like, and also a gas, for example air, nitrogen, a noble gas, mixtures of gases and/or the like, and also a combination of these.

The drive fluid can typically be made available exclusively with the console. For this purpose, for example, the console can accommodate a drive pressure sensor, with which the drive pressure of the drive fluid can be detected. By virtue of the fact that the drive pressure sensor can be provided on the console side, and because it does not need to come into contact with the treatment fluid, it does not have to meet any particular requirements as regards sterility. Therefore, the drive pressure sensor can be chosen and optimized in terms of its detection functionality.

Moreover, a position sensor is typically provided, which serves to detect the position of the elastic partition element. The position sensor can be provided either in the console or in the cassette. The position sensor can detect the position of the partition element typically in a contactless manner. For this purpose, for example, it can have an inductive, capacitive or also optical sensor element. The position sensor can communicate with the control device of the ophthalmosurgical system wirelessly, for example by radio, or also via a communication line. The position sensor can be configured, for example, as a transponder, in particular as a passive transponder, as a result of which a cassette-side energy supply can be omitted or reduced, if the position sensor is provided in the console.

In the context of the method implementation, provision is made that the drive fluid is subjected to a first drive pressure, at which the elastic partition element adopts a first position. This position is typically a position of the partition element in which a pressure difference caused by the partition element is as small as possible. That is to say, in this first position the drive pressure can be chosen such that the partition element is substantially or almost in the relaxed state. In this state of the partition element, a pressure difference between the drive chamber and the pump chamber can typically be largely ignored. In this first position of the partition element, a prevailing pressure of the treatment fluid can be detected with a detection sensor of the ophthalmosurgical system. In principle, the detection sensor can of course be configured as a pressure sensor or the like, which makes it possible to reliably detect the pressure of the treatment fluid. For this purpose, the detection sensor can be arranged at least partially on the cassette side, so that access to the treatment fluid is possible. The detection sensor can therefore be arranged at least partially on the cassette side. However, it can also be arranged at least partially on the console side, as will be explained in more detail below.

The drive fluid is then, typically thereafter, subjected to at least one further drive pressure, which is different from the first drive pressure and at which the partition element adopts a further position different from the first position. At this further or second drive pressure, different from the first drive pressure, a further or second position of the partition element is adopted. In this further or second position, a further pressure of the treatment fluid is detected, specifically with the detection sensor. Typically, the respective positions of the partition element are also detected with the position sensor.

The treatment fluid pressures present in at the respective positions and the drive pressures present in the respective positions are then taken into account in the operation of the fluid pump. The operation of the fluid pump can include an evaluation of the detected pressures and positions, and specific dependencies of the aforementioned variables, applicable to the respective fluid pump, can then be determined. Typically, the operation permits determination of a dependency in which a pressure difference, brought about by the partition element, is dependent on its respective position. This dependency can then be utilized for the regulation of the ophthalmosurgical system, in particular of the at least one fluid pump. The evaluation can be carried out at least partially with the control device of the ophthalmosurgical system.

To achieve the first position of the partition element, the partition element can typically be brought to a rest position. The rest position can be the relaxed position of the partition element, in which it transmits hardly any force between the drive chamber and the pump chamber, that is to say between the drive fluid and the treatment fluid in the respective chamber of the fluid pump. In addition, provision can be made that, in order to reach at least one further position of the partition element, the partition element is deflected to a maximum extent. This exemplary embodiment makes it possible to detect the behaviour of the fluid pump during an entire pump stroke.

Of course, the method according to an aspect of the disclosure is not restricted to the use of only two different drive pressures and positions of the partition element at which corresponding pressures of the treatment fluid are detected. Depending on requirements and on the properties of the fluid pump, it is of course possible here to also provide a plurality of different drive pressures and positions of the partition element, at each of which a respective pressure of the treatment fluid is detected. The operation of the fluid pump can be further improved in this way. The choice of the different drive pressures and positions of the partition element does not need to be provided equidistantly. Depending on requirements, a difference between two successive drive pressures and positions of the partition element can vary.

According to a further development, it is provided that, in a flow path for the treatment fluid, formed between the fluid pump and a surgical instrument, a controllable adjustment mechanism is arranged which, when one of the aforementioned positions is reached by the partition element, is switched to a state that reduces or blocks the flow of the treatment fluid. The adjustment mechanism can be an at least partially separate mechanism or can also be made available at least partially by the ophthalmosurgical system. Typically, the adjustment mechanism is controlled with the control device. The adjustment mechanism makes it possible to control a flow of the treatment fluid. For example, provision can be made that the flow is throttled or blocked during the detection of the pressure of the treatment fluid.

This exemplary embodiment makes it possible to improve the detection of the pressure of the treatment fluid. In particular, provision can be made that, at a transition from the first drive pressure to the further drive pressure, the adjustment mechanism is switched to an at least partially or typically completely opened state, such that a corresponding change of the position of the partition element can be permitted, and, when the further drive pressure is reached, the adjustment mechanism is switched to the state reducing or throttling or blocking the flow of the treatment fluid, such that the corresponding pressure of the treatment fluid can be reliably detected with the detection sensor. For this purpose, the adjustment mechanism can have a valve for example, which is adjustable with a suitable drive. For example, the valve can be actuated with an electric lifting magnet or the like. However, provision can also be made that the adjustment mechanism can be driven pneumatically or hydraulically. The adjustment mechanism can also include the cassette. For example, if a fluid pump for conveying the irrigation fluid and a further fluid pump for conveying the aspiration fluid are provided in the cassette, the instrument-side flow paths of the two fluid pumps can be fluidically connected to each other, such that, in order to operate one of the fluid pumps, the other of the fluid pumps, in particular the inlet valve or outlet valve thereof, can serve as adjustment mechanism. For this purpose, for example, corresponding valves of the fluid pumps can be actuated. The control of the elements can be effected at least partially with the control device.

The surgical instrument can serve for treating the eye. For example, it can be a handpiece for performing a phacoemulsification. The surgical instrument can, for example, be attachable as a separate part to the ophthalmosurgical system or can also be a constituent part of the ophthalmosurgical system. Typically, the surgical instrument can be supplied with the treatment fluid with the cassette. For this purpose, the surgical instrument can, for example, be directly attachable to the cassette. Provision can be made that, as treatment fluid, an irrigation fluid is delivered to the surgical instrument and/or an aspiration fluid is removed from the surgical instrument It is additionally provided that, at a respective position, a respective pressure difference between the respective drive pressure and the detected pressure of the treatment fluid is determined, in order to determine how a pressure difference, effected by the elastic partition element, between the respective drive pressure and the respective pressure of the treatment fluid is dependent on the position. In this way, it is possible to determine a particularly relevant dependency for the regulation in the context of the calibration of the fluid pump. The method described above can be used for this purpose.

It is further provided that, arranged in a flow path formed between the fluid pump and the surgical instrument of the ophthalmosurgical system, there is an elastic membrane which contacts the treatment fluid and, depending on a pressure of the treatment fluid, exerts a force on a force sensor associated with the membrane, in order to form the detection sensor with which the pressure of the treatment fluid is detected. In this way, the pressure of the treatment fluid can be detected without using a pressure sensor. In addition, this design of the detection sensor means that the force sensor can be arranged on the console side and the membrane on the cassette side, such that the force sensor does not need to come into contact with the treatment fluid. In addition, the cassette can in this way be configured very simply in order to be able to detect the pressure of the treatment fluid. The membrane can, for example, be arranged on a fluid line for the treatment fluid, to which line the surgical instrument can also be attached. In this way, the membrane is in contact with the treatment fluid, such that a deflection of the membrane is dependent on the pressure of the treatment fluid. This deflection can be detected by the force sensor, which for example contacts the membrane, such that the pressure of the treatment fluid can be inferred by evaluation of the detected force. This exemplary embodiment also proves advantageous because the cassette is generally provided as a disposable part for a single use, and therefore resources can be saved, in particular as regards the force sensor.

It is further provided that, at a predefined drive pressure, a first force is detected with the force sensor, the predefined drive pressure is altered by a predefined pressure change value, and a second force is detected with the force sensor, wherein the predefined pressure change value is less than about 50%, typically less than about 20%, of the predefined drive pressure. This further development allows the detection sensor, here formed by the membrane and the force sensor, to be used with great precision, such that it can then be utilized again for the operation of the fluid pump. Typically, provision is also made here that the partition element is in the range of the relaxed state. This can be achieved, for example, by the fact that a fluid line, to which the surgical instrument is attachable, is open towards its end. However, provision can also be made that the corresponding fluid line can be closed with the force sensor.

Starting from the predefined drive pressure, the drive pressure altered by the predefined pressure change value can be set, wherein the force that changes dependently thereon is then detected with the force sensor. From the data obtained in this way, the function of the force sensor can then be determined. This method implementation can typically also be carried out at least partially with the control device. Although this method implementation is particularly suitable to be used in the range of the relaxed state of the partition element, this method implementation is not however limited thereto. In principle, this method implementation can of course also be carried out with partition elements that are not relaxed. However, this has effects on the determination of the function of the detection sensor comprising the force sensor and the membrane. The predefined pressure change value is typically less than about 50%, typically less than about 20%, of the indicated drive pressure. Thus, the function of the detection sensor can be determined with minimal changes of the drive pressure. In particular, it is possible that the partition element does not need to leave the range of the relaxed state during this method implementation. The force sensor can be utilized to obtain a redundancy with respect to the treatment fluid.

It proves particularly advantageous if, for operating purposes, the pressure of the treatment fluid can be determined with the force sensor. Since the force sensor does not need to be arranged in the cassette, the force sensor can thus be optimized in terms of its force detection functionality. Therefore, it does not have to meet any requirements as regards sterility. By contrast, the sterility as regards the treatment fluid can be ensured through the provision of the membrane on the cassette. In this way, the pressure of the treatment fluid can be detected in a sterile and at the same time reliable manner.

It is further provided that the method according to an aspect of the disclosure is carried out in an operation of the fluid pump that differs from its intended operation. The operation can be carried out, for example, when the fluid pump is not in use during the treatment of an eye. For example, the method can be carried out before the start of an intended use, in particular before a surgical procedure on an eye. However, the method can also be carried out during interruptions in the treatment or the like. Provision can also be made that the calibration is repeated at predefined time intervals or at predefined events. For example, such an event can be a replacement of the surgical instrument or the like.

As regards a method for operating an ophthalmosurgical system for treating an eye, it is further provided that the method of the disclosure for operating the fluid pump is started after the cassette has been inserted into the console. It can start, for example, in an automated manner with the insertion of the cassette. In addition, provision can also be made that the method is started by manual actuation by the user of the ophthalmosurgical system. Of course, combinations of these may also be provided.

The ophthalmosurgical system for treating an eye has at least one console for accommodating a treatment fluid container for receiving a treatment fluid. For example, the treatment fluid container can be an irrigation fluid container which has a sufficiently large capacity for an irrigation fluid to ensure that even quite a lengthy surgical procedure can be carried out without replacing the treatment fluid container. In principle, the same can also be provided for a treatment fluid container which serves to receive the aspiration fluid. Moreover, the ophthalmosurgical system has the cassette, insertable into the console, for steering the treatment fluid to the surgical instrument for treating the eye. The cassette is typically configured in such a way that the treatment fluid does not come into contact with the console. The cassette can be configured as a disposable part, such that, after it has been used in a surgical procedure on an eye, it can be replaced for a subsequent surgical procedure. Sterility can thus be produced in a simple way. Moreover, the ophthalmosurgical system has at least one fluid pump for conveying the treatment fluid in the intended operation of the system. Typically, at least one fluid pump is provided for conveying the irrigation fluid and at least one pump is provided for conveying the aspiration fluid. Each fluid pump has a pump chamber, and a drive chamber separated from the pump chamber with the elastic partition element. The drive chamber can be acted upon by the drive fluid, which can be delivered to the drive chamber on the console side. For this purpose, a source of drive fluid can be provided that is configured to be adjustable in terms of the drive pressure. The drive pressure can be detected with a drive pressure sensor, which likewise can be arranged on the console side. With this embodiment of the fluid pump, it is possible that the treatment fluid can be guided in the cassette substantially separate from the console. Only attachments for delivery of the treatment fluid to the fluid pump and for removal of the treatment fluid from the fluid pump need to be provided on the cassette.

The ophthalmosurgical system further includes a position sensor for detecting the position of the elastic partition element. The position sensor is typically arranged on the cassette side, such that the pump chamber, with the elastic partition element and the position sensor, can form one unit in the cassette. For communication purposes, the position sensor can typically be coupled wirelessly to the console, in particular to the ophthalmosurgical system control device arranged typically in the console.

The console can additionally include the control device which can realize the required functions for the intended operation and also in particular for the method implementations according to the disclosure. For this purpose, the control device can be attached to the corresponding sensors and drive and control elements.

The advantages and effects indicated for the method according to an aspect of the disclosure are of course also equally applicable to the ophthalmosurgical system according to an aspect of the disclosure, and the method for its operation, and vice versa. In principle, therefore, device features can thus also be formulated as method features, or vice versa.

Further features of the disclosure will become clear from the figures and the description of the figures. The features and combinations of features mentioned in the description above and the features and combinations of features mentioned in the description of the figures below and/or shown only in the figures may be used not only in the respectively specified combination but also in other combinations, without departing from the scope of the disclosure. Hence, exemplary embodiments of the disclosure which are not explicitly shown and explained in the figures, but which emerge and are producible by way of separated combinations of features from the explained embodiments, should also be considered to be encompassed and disclosed. Disclosure shall also be considered to extend to exemplary embodiments and combinations of features that thus do not have all the features of an independent claim as originally worded. Furthermore, disclosure shall be considered to extend to exemplary embodiments and combinations of features, especially via the embodiments set out above, that go beyond or depart from the combinations of features set out in the dependency references of the claims.

BRIEF DESCRIPTION OF THE DRAWINGS

The disclosure will now be described with reference to the drawings wherein:

FIG. 7 shows a schematic illustration of a first fluid pump with a first detection sensor of the ophthalmosurgical system according to according to the first exemplary embodiment the disclosure.

DESCRIPTION OF EXEMPLARY EMBODIMENTS

Figure 1:
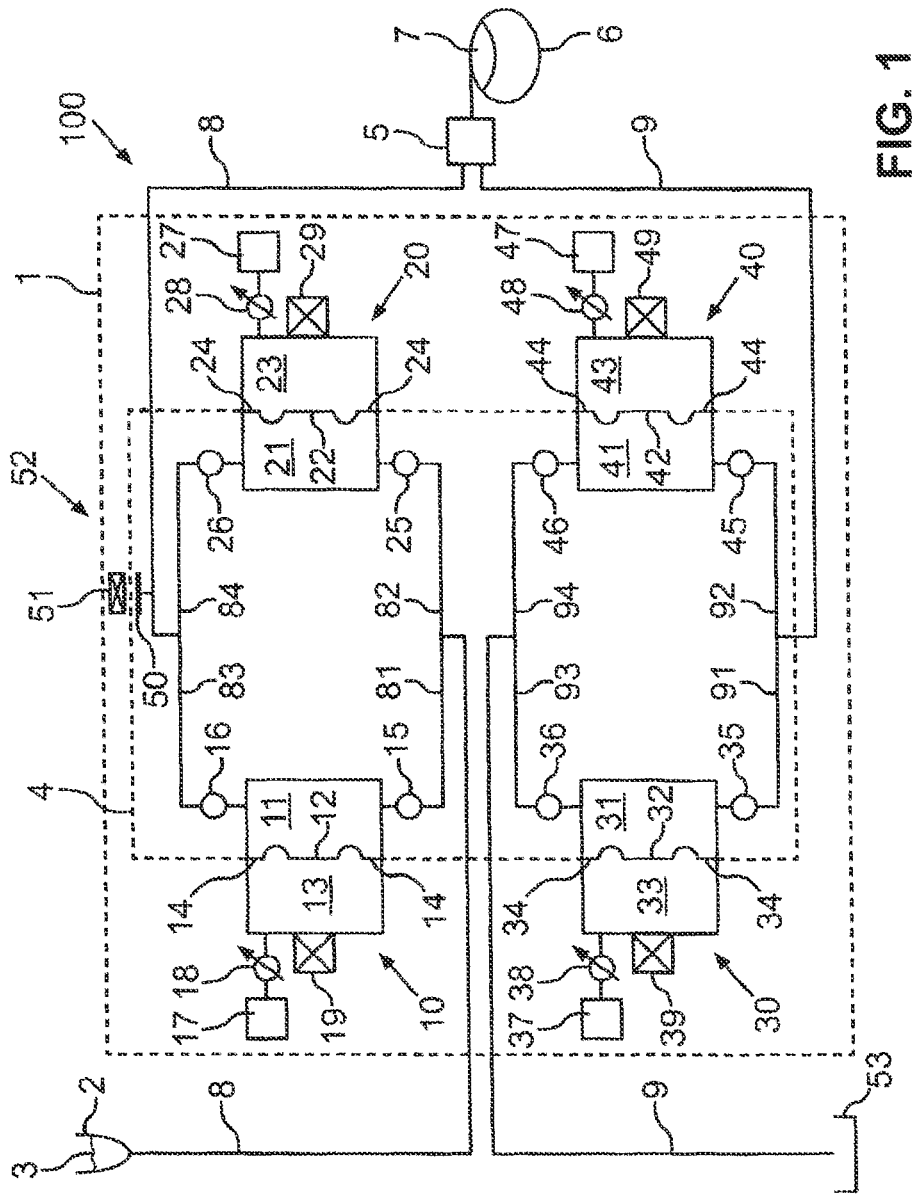
FIG. 1 shows a schematic illustration of the ophthalmosurgical system according to a first exemplary embodiment of the disclosure.
Figure 2:
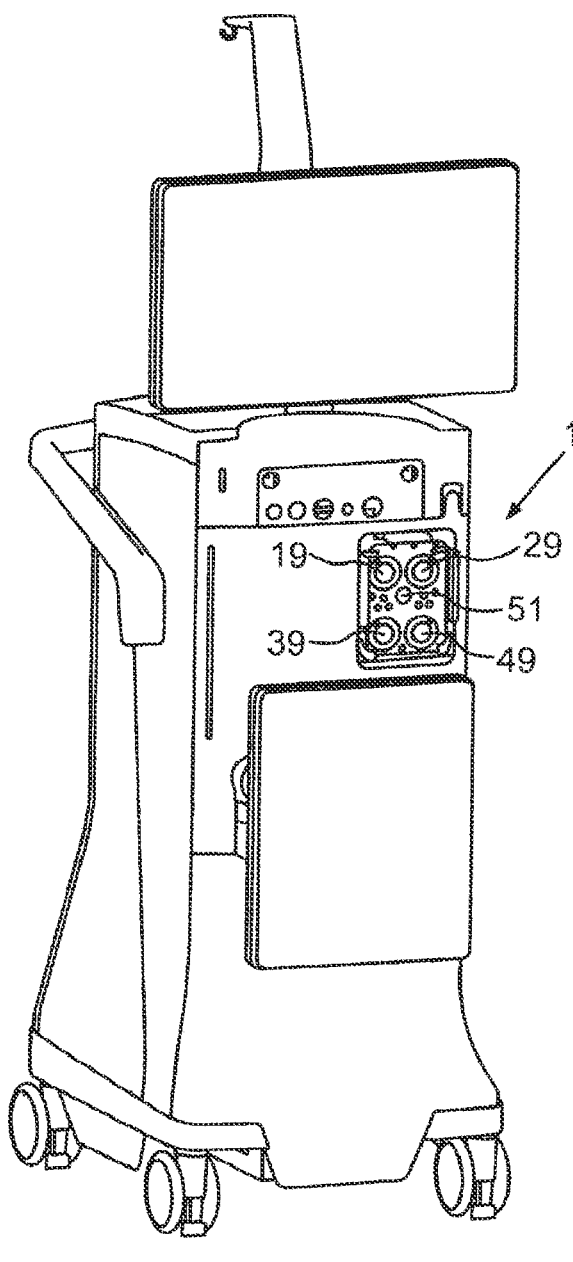
FIG. 2 shows a schematic perspective illustration of a console of the system according to FIG. 1.
Figure 3:
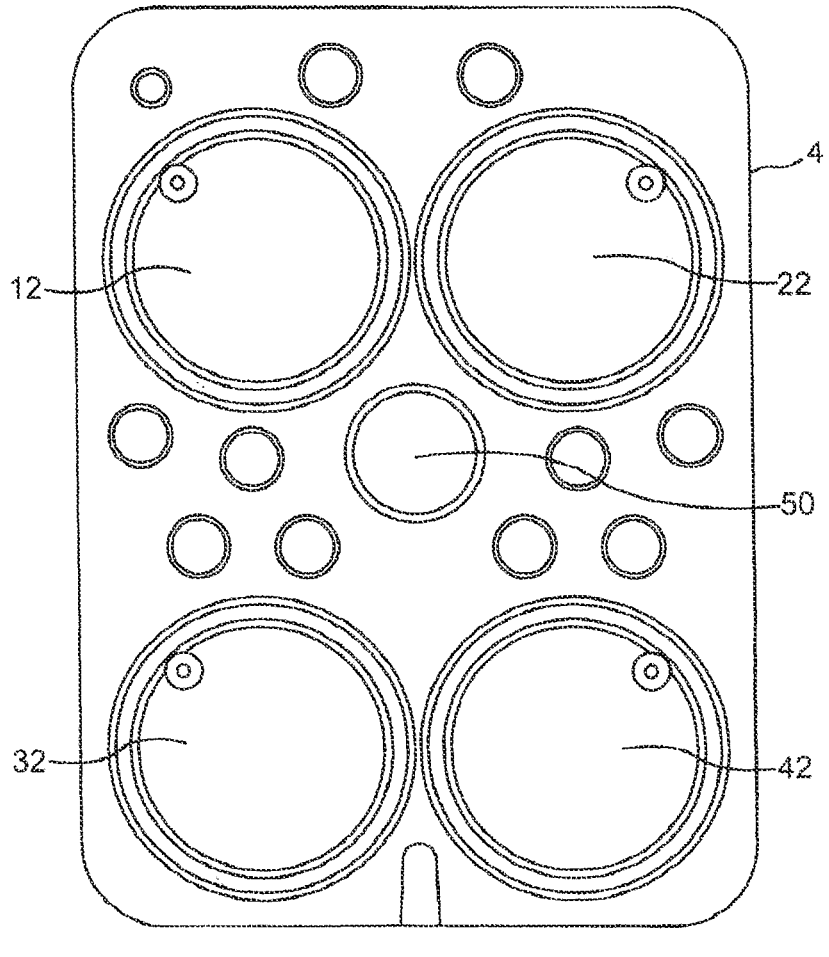
FIG. 3 shows a schematic plan view of an attachment side of a cassette for the system according to FIG. 1.

FIG. 1 shows a schematic illustration of an ophthalmosurgical system 100 according to a first exemplary embodiment the disclosure. The system 100 has a console 1, to which an irrigation fluid container 2 with an irrigation fluid 3 contained therein is coupled. In addition, the system 100 has a cassette 4 which is insertable into the console 1. In addition to conveying the irrigation fluid 3 to a surgical instrument 5 which serves for phacoemulsification of a lens 7 of an eye 6 as treatment, the cassette also serves for removing a resulting aspiration fluid from a treatment region of the eye 6. In the present case, the surgical instrument 5 is configured as a handpiece and serves for the phacoemulsification of the lens 7 of the eye 6. FIG. 2 shows a schematic perspective illustration of the console 1 without the cassette 4. FIG. 3 shows a schematic plan view of an attachment side of the cassette 4 for connection to the console 1.

The system 100 further includes an irrigation fluid flow path 8, which runs from the irrigation fluid container 2 to the surgical instrument 5 via the cassette 4. In addition, the system 100 has a first fluid pump 10 with a first pump chamber 11, and a first drive chamber 13 separated therefrom by a first elastic partition element 12. The first elastic partition element 12 has an edge 14, with which it is arranged fixedly in the fluid pump 10.

The irrigation fluid 3 can be delivered to the first pump chamber 11 via the irrigation fluid flow path 8 and a first inlet valve 15 of the first pump chamber 11, depending on a valve state of the inlet valve 15. Moreover, it can be removed from the pump chamber 11 again via an outlet valve 16, depending on the valve state of the latter. The first drive chamber 13 can be acted upon by a first drive fluid 17, which can be delivered with a proportional valve 18 arranged in the console 1. Depending on a differential pressure between the first drive fluid 17 in the first drive chamber 13 and the irrigation fluid 3 as treatment fluid in the first pump chamber 11, there is an elastic deformation or deflection of the first elastic partition element 12. A magnitude of the pressure in the first drive chamber 13 is larger than a magnitude of the pressure in the first pump chamber 11. When the inlet valve 15 is closed and the outlet valve 16 opened, the irrigation fluid 3 can flow out of the first pump chamber 11 into a subsidiary path 83 attached to the outlet valve.

The position of the first elastic partition element 12 can be detected with a first position sensor 19, which is arranged outside the first fluid pump 10, for example in the console 1. The first position sensor 19 can be configured, for example, as an inductive or capacitive displacement sensor.

As will be seen from FIG. 1, the drive chamber 13 is arranged in the console 1, and the pump chamber 11 with the partition element 12 is arranged in the cassette 4. In this way, by arranging the cassette 4 in the console 1, the fluid pump 10 is completed.

It can also be seen from FIG. 1 that a second fluid pump 20 is fluidically connected in parallel to the fluid pump 10. In the present case, the fluid pump 20 is configured like the fluid pump 10. Therefore, the irrigation fluid flow path 8 in the cassette 4 is divided into a first subsidiary path 81 and a second subsidiary path 82. The first subsidiary path 81 is attached to the first inlet valve 15, and the second subsidiary path 82 is attached to a second inlet valve 25 of the second fluid pump 20.

The second fluid pump 20 has a second pump chamber 21, and a second drive chamber 23 separated from the latter with a second elastic partition element 22. The partition element 22 has a second edge 24, which is mounted fixedly in the second fluid pump 20. The second drive chamber 23 can be acted upon by a second drive fluid 27 via a second proportional valve 28 arranged in the console 1. A position of the partition element 22 can be detected with a position sensor 29. By way of a second outlet valve 26, the irrigation fluid 3 can again leave the second pump chamber 21 into the subsidiary path 84. By way of the subsidiary paths 83, 84, which are attached to the first and second outlet valve 16, 26 respectively, the irrigation fluid 3 leaving the respective fluid pump 10, 20 can be delivered again to the irrigation fluid flow path 8, in order to be delivered to the instrument 5.

In a region of the fluidic connection of the subsidiary path 83 to the subsidiary path 84, for example in the downstream irrigation fluid flow path 8, an elastic membrane 50 is formed which is able to contact the irrigation fluid 3. The membrane 50 is arranged at the cassette 4. The membrane 50 is contacted by a force sensor 51, which for its part is arranged in the console 1. The membrane 50, in conjunction with the force sensor 51, forms a detection sensor 52.

During the fragmentation of the crystalline lens 7, small lens particles are released and can be aspirated together with the delivered irrigation fluid 3. The irrigation fluid 3, contaminated with lens particles, is then referred to as aspiration fluid and is conveyed via an aspiration fluid flow path 9 to an aspiration fluid collection container 53. For this purpose, two further fluid pumps 30, 40 connected in parallel can be provided which, in principle, are of a design comparable to the fluid pumps 10, 20 for the irrigation fluid. For this purpose, provision is made inside the cassette 4 that the aspiration flow path 9 likewise divides into two subsidiary paths 91, 92, which are attached via respective inlet valves 35, 45 to the respective fluid pumps 30, 40, specifically here to the respective pump chambers 31, 41. Here too, the pump chambers 31, 41 are separated from respective drive chambers 33, 43 by respective elastic partition elements 32, 42. The partition elements 32, 42 have respective edges 34, 44, which are mounted fixedly in the respective fluid pump 30, 40. By way of respective outlet valves 36, 46 and the subsidiary paths 93, 94 attached thereto, the aspiration fluid can then be removed via the aspiration fluid flow path 9. A third drive fluid 37 can be guided to the third drive chamber 33 with a third proportional valve 38. Correspondingly, a fourth drive fluid 47 can be guided to a fourth drive chamber 43 with a fourth proportional valve 48. The proportional valves 38, 48 are arranged in the console 1. The positions of the partition elements 32, 42 can be detected with respective position sensors 39, 49. In the present case, the two fluid pumps 30, 40 are likewise operated alternately like the fluid pumps 10, 20.

Figure 4:
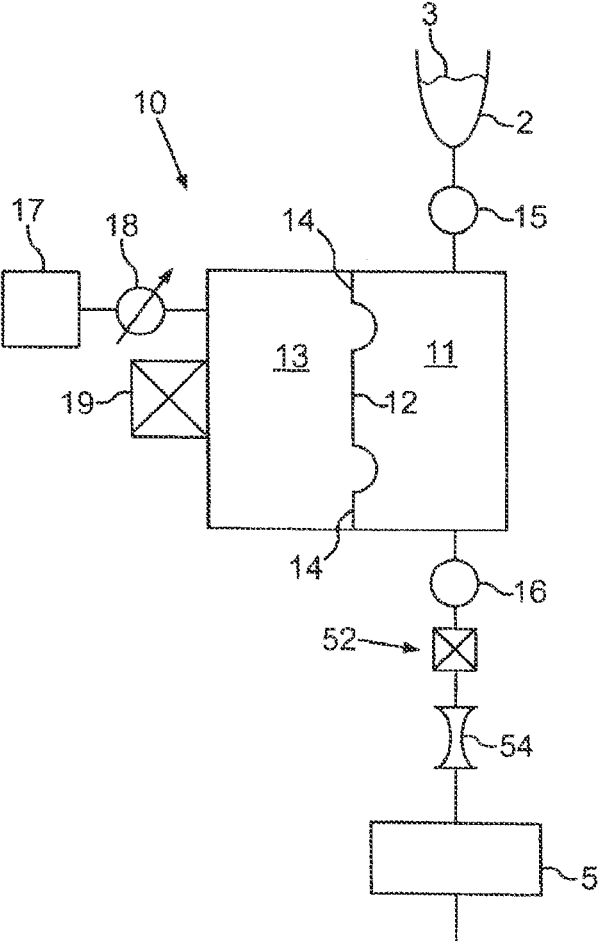
FIG. 4 shows a schematic illustration of the system according to a second exemplary embodiment of the disclosure.

FIG. 4 shows a schematic illustration of an individual fluid pump 10 of a further exemplary embodiment, which in principle corresponds to the set-up of the fluid pump 10 according to FIG. 1, as has already been explained with regard to the first exemplary embodiment, for which reason reference is additionally made to the relevant observations. In contrast to the first exemplary embodiment, the detection sensor 52 in this exemplary embodiment is attached to an adjustment mechanism 54, which in the present case is formed by an electrically actuatable shut-off valve. The adjustment mechanism 54 is arranged downstream before the surgical instrument 5.

The calibration of the fluid pump 10 will be explained below with reference to FIG. 4, and this explanation also applies to the fluid pumps 10 to 40 of the first exemplary embodiment according to FIG. 1.

Each of the fluid pumps 10 to 40 serves to convey the respective treatment fluid, which in the present case is the irrigation fluid 3 or the aspiration fluid. It has been found that the properties of the fluid pump 10 to 40 are dependent, inter alia, on the respective partition elements 12 to 42, the mechanical behaviour of which may vary considerably from fluid pump to fluid pump. However, the properties of the fluid pumps 10 to 40 need to be known in order to regulate as precisely as possible the delivery of irrigation fluid to the instrument 5 and in order to remove aspiration fluid as precisely as possible. Precise regulation is intended to ensure, among other things, that an intraocular pressure, particularly in a capsular bag, is as constant as possible during the treatment, so that the capsular bag, which holds the lens to be removed, is stressed as little as possible. This can be achieved by the operation of the respective fluid pumps 10 to 40.

Figures 5, 6:
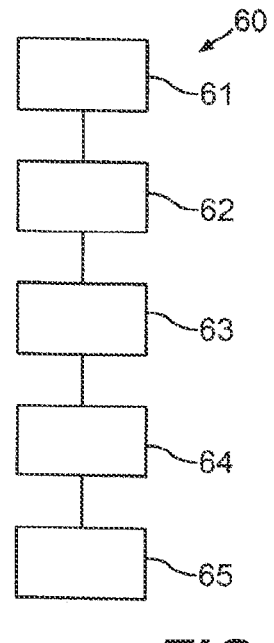
FIG. 5 shows a schematic illustration of a flow chart for a method implementation according to the disclosure.
FIG. 6 shows a schematic diagram of how, in the context of the calibration of a fluid pump according to FIG. 4, a pressure difference at a partition element is dependent on a position of the partition element.

To operate the fluid pump 10 according to FIG. 4, in the present case a method implementation is provided as per the schematic flow chart 60 according to FIG. 5. In a first step 61, the drive fluid 17 is set with the proportional valve 18 inside the drive chamber 13 to a predefined first drive pressure, at which the elastic partition element 12 adopts a first position. The first position is detected with the position sensor 19. A pressure of the treatment fluid, here of the irrigation fluid 3, present in the first position of the partition element 12 is detected in a second step 62 with a detection sensor 52 of the ophthalmosurgical system 100. Then, in a third step 63, the drive fluid 17 is subjected via the proportional valve 18 to a further drive pressure, which is different from the first drive pressure and at which the partition element 12 adopts a further position which is different from the first position and which is likewise detected with the detection sensor 52. The further position of the partition element 12, brought about by the further drive pressure, and a further treatment fluid pressure present in this further position, are detected in a fourth step 64. The data acquired here are transmitted to a control device (not shown) of the ophthalmosurgical system 100, which control device, in a fifth step 65, takes the treatment fluid pressures present in the respective positions, and the drive pressures present in the respective positions, into account in the operation of the fluid pump 10.

Depending on requirements, a plurality of different drive pressures can be set in order to detect respective positions of the partition element 12 and respective pressures of the treatment fluid. One position of the partition element 12 is typically a rest position. A further position of the partition element 12 can be a position in which the partition element 12 is deflected to a maximum extent. It is in this way possible to achieve a complete calibration of the fluid pump 10 over the entire stroke range.

With the adjustment mechanism 54, the flow of the treatment fluid can be blocked when an aforementioned position is reached by the partition element 12. The flow can be blocked, for example, for a predefined short time period, for example of less than about 1.5 seconds, typically less than about 0.9 second, such that a detection of the respective sensor values can be reliably performed.

The evaluation of the data can include the determination of a respective pressure difference between the respective drive pressure and the detected pressure of the treatment fluid in a respective position of the partition element 12, in order to determine how a pressure difference, effected by the elastic partition element 12, between the drive pressure and the respective pressure of the treatment fluid is dependent on the position. For this purpose, provision can be made that mathematical methods, in particular regression methods or also statistical evaluation methods, are taken into consideration in order to be able to determine the dependency as reliably and as exactly as possible. On the basis of the dependency thus determined, the regulation can then be effected in the intended operation of the ophthalmosurgical system 100. An example of such an evaluation is illustrated in a schematic diagram in FIG. 6. In FIG. 6, an abscissa is assigned an electrical voltage which the position sensor 19 makes available depending on the detected position of the partition element 12. An ordinate is assigned the pressure difference at the partition element 12. A graph 56 illustrates the dependency of the pressure difference on the electrical voltage of the position sensor 19. It will be seen from FIG. 6 that the pressure difference, in the case of small deflections or positions of the partition element 12, is likewise comparatively small. This corresponds to an electrical voltage of the position sensor 19 of less than about 3 V. By contrast, starting from an electrical voltage of about 3 V, the pressure difference increases markedly. The dependency determined in the context of the operation can now be used for precise regulation in the intended operation of the ophthalmosurgical system 100. The curve determined in this way can be stored in the control device, such that it is available for performing the regulation functionality. Overall, it is possible with the disclosure that an improved, more precise regulation for the conveying of the treatment fluid can be achieved by the method.

Figure 7:
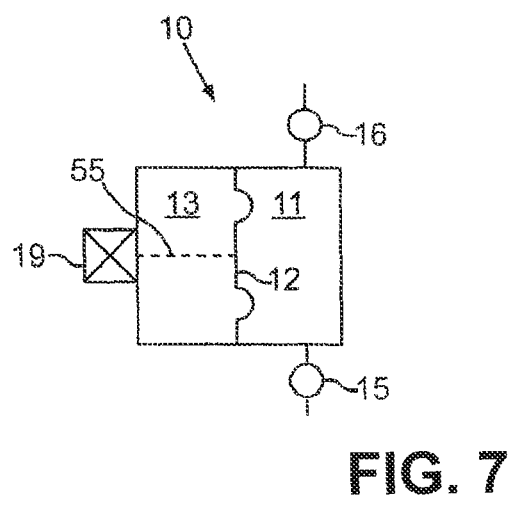

FIG. 7 shows a schematic illustration of the position sensor 19 according to FIG. 1 and according to FIG. 4. The position sensor 19 is coupled to the partition element 12 via a coupling 55. The coupling 55 can be effected, for example, using an electrical or magnetic field. Thus, depending on a respective position of the partition element 12, the position sensor 19 can make available an electrical voltage as sensor signal, as has already been explained on the basis of FIG. 6. In principle, it is of course possible to provide any detection, typically contactless detection, of the position.

To be able to operate the fluid pumps 10, 20, 30, 40 even without the adjustment mechanism 54 in FIG. 4, provision can be made that, instead of the surgical instrument 5, a fluidic short circuit is attached, which is removed again after the abovementioned method steps. In this way, during the operation of the fluid pumps 10, 20, the inlet valves 35, 45 in the aspiration fluid flow path 9 can take over the function of the adjustment mechanism 54. During the operation of the fluid pumps 30, 40, the outlet valves 16, 26 can take over the function of the adjustment mechanism 54. In this way, even with a complex ophthalmosurgical system 100 as illustrated on the basis of FIG. 1, the method according to an exemplary embodiment of the disclosure can be carried out for all the fluid pumps. By virtue of the fluidic short circuit, a single detection sensor 52 is sufficient.

In addition, provision can be made that the detection sensor 52 is also calibrated. In the present case, this is also particularly expedient, because the membrane 50 is likewise replaced when the cassette 4 is exchanged. That is to say, the combination forming the detection sensor 52, i.e., the combination of membrane 50 and force sensor 51, is likewise altered when the cassette 4 is exchanged.

To be able to take account of the changes resulting from this, provision can be made that, at a predefined drive pressure, a first force is detected with the force sensor 51, the predefined drive pressure is altered by a predefined pressure change value, and a second force is detected with the force sensor 51. Typically, the pressure change value is less than 50%, typically less than 20%, of the predefined drive pressure. For the purpose of operation, the pressure of the treatment fluid is determined with the force sensor 51. For example, a line of best fit for the detection sensor 52 can be determined, with which a detected force of the force sensor 51 can be assigned to a drive pressure.

It is understood that the foregoing description is that of the exemplary embodiments of the disclosure and that various changes and modifications may be made thereto without departing from the spirit and scope of the disclosure as defined in the appended claims.

LIST OF REFERENCE NUMERALS

1 Console
2 Irrigation fluid container
3 Irrigation fluid
4 Cassette

US 12,629,467 B2

15

16

5 Surgical instrument
6 Eye
7 Crystalline lens
8 Irrigation fluid flow path
9 Aspiration flow path
10 Fluid pump
11 Pump chamber
12 Partition element
13 Drive chamber
14 Edge
15 Inlet valve
16 Outlet valve
17 Drive fluid
18 Proportional valve
19 Position sensor
20 Fluid pump
21 Pump chamber
22 Partition element
23 Drive chamber
24 Edge
25 Inlet valve
26 Outlet valve
27 Drive fluid
28 Proportional valve
29 Position sensor
30 Fluid pump
31 Pump chamber
32 Partition element
33 Drive chamber
34 Edge
35 Inlet valve
36 Outlet valve
37 Drive fluid
38 Proportional valve
39 Position sensor
41 Pump chamber
42 Partition element
43 Drive chamber
44 Edge
45 Inlet valve
46 Outlet valve
47 Drive fluid
48 Proportional valve
49 Position sensor
50 Membrane
51 Force sensor
52 Detection sensor
53 Aspiration fluid collection container
54 Adjustment mechanism
55 Coupling
56 Graph
60 Flowchart
61 to 65 Step
81, 82, 83, 84, 91, 92, 93, and 94 Subsidiary path
100 Ophthalmosurgical system

What is claimed is:

1. A method for operating a fluid pump of an ophthalmosurgical system, the fluid pump being configured to convey a treatment fluid and the treatment fluid being conveyed with the fluid pump during an operation of the ophthalmosurgical system, the fluid pump having a pump chamber and a drive chamber separated from the pump chamber with an elastic partition element, the drive chamber being acted upon by a drive fluid, and a position of the elastic partition element being detected with a position sensor, the method comprising:

subjecting the drive fluid to a first drive pressure, at which the elastic partition element adopts a first position;

detecting a treatment fluid pressure present in the first position of the partition element with a detection sensor of the ophthalmosurgical system;

subjecting the drive fluid to at least one further drive pressure, which is different from the first drive pressure and at which the partition element adopts a further position different from the first position;

detecting the at least one further position of the partition element, brought about by the at least one further drive pressure, and a further treatment fluid pressure present in this further position;

arranging, in a flow path formed between the fluid pump and the surgical instrument of the ophthalmosurgical system, an elastic membrane which contacts the treatment fluid, and which, depending on a pressure of the treatment fluid, exerts a force on a force sensor associated with the membrane, and the elastic membrane and the force sensor forming the detection sensor with which the pressure of the treatment fluid is detected;

detecting, at a predefined drive pressure, a first force with the force sensor;

altering the predefined drive pressure by a predefined pressure change value;

detecting a second force with the force sensor, wherein the predefined pressure change value is less than 20% of the predefined drive pressure; and taking into account the treatment fluid pressures present in the respective positions and the drive pressures present in the respective positions in the operation of the fluid pump.

2. The method according to claim 1, wherein, in order to reach the first position of the partition element, the partition element is brought to a rest position, and/or, in order to reach at least one further position of the partition element, the partition element is deflected to a maximum extent.

3. The method according to claim 1, further comprising:

arranging, in a flow path for the treatment fluid, formed between the fluid pump and a surgical instrument, a controllable adjustment mechanism which, when one of the aforementioned positions is reached by the partition element, is switched to a state that reduces or blocks the flow of the treatment fluid.

4. The method according to claim 1, further comprising:

determining, in a respective position, a respective pressure difference between the respective drive pressure and the detected pressure of the treatment fluid, to determine how a pressure difference, effected by the elastic partition element, between the respective drive pressure and the respective pressure of the treatment fluid is dependent on the position.

5. The method according to claim 1, wherein, for the purpose of operation, the pressure of the treatment fluid is determined with the force sensor.

6. The method according to claim 1, wherein the operation is carried out in an operation of the fluid pump that differs from its intended operation.

7. A method for operating an ophthalmosurgical system for treating an eye, the ophthalmosurgical system including a console for accommodating a treatment fluid container for receiving a treatment fluid, a cassette, insertable into the console, for conveying the treatment fluid to a surgical instrument for treating the eye, and at least one fluid pump for conveying the treatment fluid during operation of the system, the fluid pump having a pump chamber and a drive chamber separated from the pump chamber with an elastic partition element, the drive chamber being acted upon by a drive fluid and a position of the elastic partition element being detected with a position sensor, the console having the drive chamber and the cassette having the pump chamber with the partition element, the method comprising:

starting the method according to claim 1 after the cassette has been inserted into the console.

8. A method for operating a fluid pump of an ophthalmo-surgical system, the fluid pump being configured to convey a treatment fluid and the treatment fluid being conveyed with the fluid pump during an operation of the ophthalmosurgical system, the fluid pump having a pump chamber and a drive chamber separated from the pump chamber with an elastic partition element, the drive chamber being acted upon by a drive fluid, and a position of the elastic partition element being detected with a position sensor, the method comprising:

subjecting the drive fluid to a first drive pressure, at which the elastic partition element adopts a first position;

detecting a treatment fluid pressure present in the first position of the partition element with a detection sensor of the ophthalmosurgical system;

subjecting the drive fluid to at least one further drive pressure, which is different from the first drive pressure and at which the partition element adopts a further position different from the first position;

detecting the at least one further position of the partition element, brought about by the at least one further drive pressure, and a further treatment fluid pressure present in this further position;

arranging, in a flow path formed between the fluid pump and the surgical instrument of the ophthalmosurgical system, an elastic membrane which contacts the treatment fluid, and which, depending on a pressure of the treatment fluid, exerts a force on a force sensor associated with the membrane, and the elastic membrane and the force sensor forming the detection sensor with which the pressure of the treatment fluid is detected;

detecting, at a predefined drive pressure, a first force with the force sensor;

altering the predefined drive pressure by a predefined pressure change value;

detecting a second force with the force sensor, wherein the predefined pressure change value is less than 50% of the predefined drive pressure; and taking into account the treatment fluid pressures present in the respective positions and the drive pressures present in the respective positions in the operation of the fluid pump.

* * * * *